United States Patent [19]

Deshpande et al.

[11] Patent Number: 4,847,076
[45] Date of Patent: Jul. 11, 1989

[54] METHOD FOR ENHANCING THE BODY OF HAIR

[75] Inventors: Vikas M. Deshpande, Ringwood; John M. Walts, Clark; Susan A. Decker, Butler, all of N.J.

[73] Assignee: Sterling Drug Inc., New York, N.Y.

[21] Appl. No.: 90,732

[22] Filed: Aug. 28, 1987

[51] Int. Cl.$^4$ .......... A61K 7/09; A61K 7/11; A45D 7/04
[52] U.S. Cl. .................. 424/71; 132/203; 424/47
[58] Field of Search .......... 424/47, 70, 71; 132/7, 132/203

[56] References Cited

U.S. PATENT DOCUMENTS

| | | | |
|---|---|---|---|
| 3,864,476 | 2/1975 | Altieri | 424/71 |
| 3,912,808 | 10/1975 | Sokol | 424/71 |
| 3,966,903 | 6/1976 | Torii et al. | 424/71 |
| 4,243,659 | 1/1981 | Balingit et al. | 424/70 |
| 4,296,764 | 10/1981 | Pallone et al. | 132/7 |
| 4,299,240 | 11/1981 | Failing | 424/71 X |
| 4,390,033 | 6/1983 | Khalil et al. | 132/7 |
| 4,391,286 | 7/1983 | Hsiung et al. | 132/7 |
| 4,416,297 | 11/1983 | Wolfram et al. | 132/7 |
| 4,426,375 | 1/1984 | Jacquet et al. | 424/70 |
| 4,504,466 | 3/1985 | Eda | 424/72 |
| 4,602,648 | 7/1986 | Syed et al. | 132/7 |
| 4,659,566 | 4/1987 | Petrow | 424/71 |

FOREIGN PATENT DOCUMENTS 2066310 12/1980 United Kingdom .

OTHER PUBLICATIONS

W. R. Markland, Norda ® Briefs, No. 492, Jul.-Aug., 1979.
CTFA Cosmetic Ingredient Dictionary, Third Edition, pages 83, 128, 209, 267-268, 278, 312.

Primary Examiner—Ellis P. Robinson
Assistant Examiner—Susan Rucker
Attorney, Agent, or Firm—Frederik W. Stonner; Paul E. Dupont

[57] ABSTRACT

A method for enhancing the body of hair comprising applying to the hair a composition comprising as essential ingredients in certain critical amounts an alkali metal or ammonium bisulfite, an alkanolamine, a guar hydroxypropyltrimonium chloride, a certain quaternary ammonium conditioner, an alkali metal or ammonium carbonate or an alkali metal phosphate when the bisulfite is alkali metal bisulfite and water; working the composition into the hair, lifting the hair with, e.g., the finger tips, a hair pick or the tail of a comb, allowing the composition to remain in contact with the hair for about 20 to 30 minutes, rinsing the hair and drying the hair.

10 Claims, No Drawings

METHOD FOR ENHANCING THE BODY OF HAIR

BACKGROUND OF THE INVENTION
1. Field of the Invention

The invention relates to a composition and method for improving the appearance and manageability of hair, more specifically to an aqueous foamable composition and method of use thereof for conditioning and enhancing the body of hair.

2. Information Disclosure Statement

Men and women with so-called "limp" hair, that is, hair which is fine and relatively thin in diameter, have considerable difficulty in styling their hair under normal conditions of shampooing, drying and conditioning. Under higher relative humidity conditions, "limp" hair can become even "more limp" and therefore more difficult to style, manage and maintain in a particular styled configuration. Such difficulties can also be encountered in the case of normal and coarse hair. The need therefore exists for a convenient means for overcoming such difficulties, more specifically, for adding volume and fullness, i.e., body, to all types of hair.

It is known that systems for the permanent cold waving of hair can improve the body of hair, but such systems generally require that the hair be wound on curlers and/or rollers to impart curls and waves thereto, a time consuming operation. Such systems employ cold permanent waving compositions which contain reducing agents such as thiols, thioglycolates, sulfites, bisulfites and sulfides. See for example the article on sulfite cold waving and hair straightening by W. R. Markland in Norda ® Briefs, No. 492, July-August, 1979. Generally such cold permanent waving compositions are used in conjunction with rollers or rods in order to form curls or waves. Such compositions are employed in an amount, and left in contact with the hair for a time, sufficient to effect rupture of the disulfide linkage after which the composition is rinsed from the hair. The hair then generally is treated with a neutralizing (oxidizing) agent which results in the formation of new disulfide linkages. The cleaving of the disulfide linkages and subsequent formation of new disulfide linkages permits "permanent" shaping of the hair into desired configurations such as curls and waves. Cold permanent waving systems which employ rollers and/or curlers, a reducing agent and a neutralizing agent are described in U.S. Pat. Nos. 3,864,476, 4,296,764 and 4,659,566.

U.S. Pat. Nos. 3,966,903 and 4,504,466 describe cold permanent waving systems in which a neutralizing step is not required. The systems described in these patents also require the use of rods or curlers.

A 3-component cold permanent waving system currently in commercial use is OGILVIE Whisper Wave TM. The label contents of the three components are as follows:

Waving Lotion 3¾ FL. OZ.
Contains: Water, Sodium Bisulfite, Monoethanolamine, Sodium Carbonate, TEA-coco-Hydrolyzed Protein[a].
Neutralizer 3¾ FL. OZ.
Contains: Water, PEG-150 Distearate[b], Hydrogen Peroxide, Phosphoric Acid; Tetrasodium Pyrophosphate, Sodium Stannate.
PERM-SOFT TM ½ FL. OZ.
Contains: Water, Quaternium-26[c], Propylene Glycol, Quaternium-22[d], Lactic Acid, Sodium Laureth Sulfate, Hydroxyethyl Stearamide-MIPA,[e] Fragrance, Simethicone[f], Methylparaben, Sorbic Acid, D&C Yellow No. 10.

(a) the triethanolamine salt of the condensation product of coconut acid chloride and Hydrolyzed Animal Protein (CTFA Cosmetic Ingredient Dictionary, Third Edition, page 312)
(b) $CH_3(CH_2)_{16}CO\text{-}(OCH_2CH_2)_nO\text{-}CO(CH_2)_{16}CH_3$, n=average of 150 (CTFA Cosmetic Ingredient Dictionary, Third Edition, page 209)
(c) $RCO\text{-}NH\text{-}(CH_2)_3\text{-}N^+(CH_3)_2\text{-}CH_2CH_2OH$ $Cl^-$ (CTFA Cosmetic Ingredient Dictionary, Third Edition, page 268)
(d) 3-(D-gluconoylamino)-N-(2-hydroxyethyl)-N,N-dimethyl-1-propanaminium chloride (CTFA Cosmetic Ingredient Dictionary, Third Edition, pages 267–268)
(e) $CH_3(CH_2)_{16}CO\text{-}NH\text{-}CH_2\text{-}C(H)(CH_3)\text{-}OCH_2CH_2OH$ (CTFA Cosmetic Ingredient Dictionary, Third Edition, page 128)
(f) a mixture of dimethicone with an average chain length of 200 to 350 dimethylsiloxane units and silica gel (CTFA Cosmetic Ingredient Dictionary, Third Edition, page 278). Dimethicone is a mixture of fully methylated linear siloxane polymers end blocked with trimethylsiloxy units (CTFA Cosmetic Ingredient Dictionary, Third Edition, page 83)

In cold permanent waving hair with Ogilvie Whisper Wave TM, the hair is wound on rods, the waving lotion is then applied to the hair and allowed to remain on the hair for between 30 and 60 minutes, the hair is then rinsed well and, with the rods still in place, is treated with the neutralizer. The rods then are removed and the hair is rinsed, blotted dry, conditioned with the Perm-Soft TM and styled.

An almost inevitable result of exposing hair to waving or straightening compositions is a deterioration in tactile properties, "feel", manageability and combability of the hair due to tangling. It is therefore common practice to treat the hair with one or more conditioning agents to ameliorate the situation. Such conditioning agents are generally incorporated in the neutralizer or added after the neutralizing step, although the incorporation of certain conditioners in the reducing composition or in a composition for application to the hair prior to the reducing step have been described. See U.S. Pat. Nos. 3,912,808, 4,390,033, 4,391,286, 4,416,297, 4,426,375 and 4,602,648 and UK Patent Application GB 2066310 A.

U.S. Pat. No. 4,243,659 describes compositions for improving hair body comprising an aqueous solution of a hair cleansing synthetic detergent containing a bisulfite salt and dimethylurea as a hair swelling agent. The compositions preferrably contain a cationic hair conditioner. The method of using the composition involves applying it to the hair after a preliminary shampoo and rinse with the composition, allowing it to remain on the hair for from 3 to 20 minutes, rinsing it from the hair, and drying the hair and then styling it.

SUMMARY OF THE INVENTION

This invention resides in the discovery of a composition comprising a bisulfite salt, an alkanolamine, an alkalizing agent, a combination of specific cationic conditioning agents and water which when used to treat hair in accordance with a specific process, provides added volume and fullness, i.e., body, to all types of hair without the need to resort to rollers or curlers, while at the same time conditioning the hair. This added volume and fullness lasts for a period of four to six weeks.

In one aspect of the invention there is provided a composition for enhancing the body of hair comprising (a) from about 5 to about 10 percent by weight of an alkali metal bisulfite or ammonium bisulfite; (b) from about 2 to about 5 percent by weight of a mono-, di- or tri-alkanolamine; (c) from about 0.1 to about 1.5 percent by weight of guar hydroxypropyltrimonium chloride having a viscosity of 75 to 150 cps or a guar hydroxypropyltrimonium chloride having a viscosity of 2500 to 3200 cps; (d) from about 0.2 to about 1 percent by weight of a quaternary ammonium compound selected from the group consisting of a compound conforming to the formula:

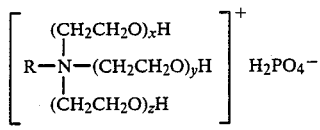

wherein x+y+z has an average value of 10 and R is a straight-chain alkyl radical having from 6 to 18 carbon atoms or mixtures of such radicals, laurdimonium hydrolyzed animal collagen, cocodimonium hydrolyzed animal collagen and steardimonium hydrolyzed animal collagen; and (e) water sufficient to make 100%; provided that when (a) is alkali metal bisulfite, the composition additionally comprises (f) from about 0.75 to about 3 percent by weight of an alkali metal carbonate, ammonium carbonate or an alkali metal phosphate.

In a second aspect of the invention there is provided a method for enhancing the body of hair which comprises, in sequence, the following steps : (1) applying to the hair the composition described above; (2) working the composition into the hair until the composition is distributed throughout the hair; (3) lifting the hair, (4) allowing the composition to remain in contact with the lifted hair for from about 20 to about 30 minutes; (5) rinsing the hair with water sufficient to remove the composition from the hair; and (6) drying the hair.

The composition of the invention, when applied to hair, swells individual hair fibers, increases the frictional coefficient and surface roughness of the hair thereby increasing hair volume and also provides conditioning to the hair, and when used in accordance with the method of the invention, enhances the body (fullness) of the hair to an unexpected degree. Thus the composition and method of the invention provide a convenient one-step procedure, i.e., as opposed to procedures involving two or more steps wherein subsequent treatment of the hair with further compositions such as neutralizers and conditioners is required, for enhancing the body of the hair while at same eliminating the need for using such devices as rollers and rods.

DETAILED DESCRIPTION OF THE INVENTION INCLUDING THE PREFERRED EMBODIMENTS

The composition of the invention comprises as essential ingredients in critical amounts a water-soluble bisulfite salt, an alkanolamine, two quaternary ammonium compounds, water and, when the bisulfite salt is an alkali metal bisulfite, a carbonate or phosphate buffering agent.

Bisulfite Salt

The bisulfite salt is selected from alkali metal bisulfites, such as sodium and potassium bisulfite, and ammonium bisulfite and mixtures thereof. The bisulfite functions as a reducing agent which chemically ruptures the disulfide linkages of cystine present in hair. The bisulfite salts are active at low to moderate temperatures (20°-45° C.), essentially odorless and can be formulated into the composition of the invention over a wide range of pH. The bisulfite salt is employed at a concentration of from about 5 to about 10 percent by weight of the composition.

Alkanolamine

The alkanolamine is selected from mono-, di- and tri-alkanolamines, wherein alkanol is straight or branched and has from 1 to 3 carbon atoms, for example monoethanolamine, diethanolamine, triethanolamine, isopropanolamine and diisopropanolamine and mixtures thereof. The alkanolamine is an alkalizing agent which functions to adjust the pH of the composition of the invention. The pH of the composition should be in the range of about 6.8 to about 10. The alkanolamine also accelerates the chemical rupture of the disulfide linkages by penetrating and swelling the hair fibers thus facilitating entrance of the bisulfite reducing agent into the hair cuticle. The alkanolamine is employed at a concentration of from about to about 5 percent by weight of the composition.

Quaternary Ammonium Compounds

The composition of the invention comprises two quaternary ammonium compounds, both of which function as hair conditioners and one of which additionally functions as a thickening agent.

The quaternary ammonium compound which functions as a hair conditioning agent as well as a thickening agent is a cationic guar gum having the CTFA adopted name "guar hydroxypropyltrimonium chloride". In the CTFA Cosmetic Ingredient Dictionary, Third Edition (hereafter "CTFA Dictionary"), page 117, guar hydroxypropyltrimonium chloride is defined as a quaternary ammonium derivative of "hydroxypropyl guar" which in turn, at page 128, is defined as a propylene glycol ether of "guar gum". Guar gum, is a galactomannan with a structure composed of a straight backone chain of D-mannopyranose units with a side branching unit of D-galactopyranose on every other unit. The average molecular weight of guar gum is in the range of 200,000 to 300,000. Two specific guar hydroxypropyltrimonium chlorides are employed in the composition of the invention. One has a viscosity of from 75 to 150 cps (1% aqueous solution ≃25° C., using a Brookfield RVF ≃20 RPM) and a pH of 9 to 11 (1% aqueous solution) and the other viscosity of from 2500 to 3200 cps (1% aqueous solution ≃25° C., using a Brookfield RVF ≃20 RPM) and a pH of 7.5 to 11 (1% aqueous solution). The guar hydroxypropyltrimonium chloride having the lower viscosity is preferred at lower pH values of the composition and the one having the higher viscosity is preferred at the higher pH values. These guar hydroxypropyltrimonium chlorides are sold under the designations respectively Jaguar C-15 and Jaguar C-17, by Celanesse Plastics and Specialties Company. Mixtures of these guar hydroxypropyltrimonium chlorides may be used. The guar hydroxypropyltrimonium chloride is employed at concentrations of from about 0.1 to about 1.5 percent by weight based on the total weight of the composition.

The upper limit of concentration in the composition of the guar hydroxypropyltrimonium chloride is governed by the degree of thickening to be imparted to the composition. As a result, the range of concentrations at which it may be employed, as defined above, is not fully adequate to provide the desired degree of hair conditioning. It is therefore essential to augment conditioning with a second conditioner which is compatible with the guar hydroxypropyltrimonium chloride.

The second conditioner is selected from a quaternary ammonium compound selected from a compound conforming to the formula:

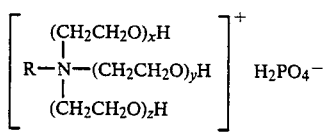

wherein $x+y+z$ has an average value of 10 and R is a straightchain alkyl radical have from 6 to 18 carbon atoms or mixtures of said alkyl radicals, laurdimonium hydrolyzed animal collagen, cocodimonium hydrolyzed animal collagen and steardimonium hydrolyzed animal collagen and mixtures thereof. The CTFA Adopted Name for the compound of Formula I is Quaternium-52 which is defined in the CTFA Dictionary as for Formula I above. Quaternium-52 is sold under the designation DEHYQUART SP by Henkel Corporation. Laurdimonium hydrolyzed animal collagen, cocodimonium hydrolyzed animal collagen (CTFA Adopted Name) and steardimonium hydrolyzed animal collagen (CTFA Adopted Name) are multi-functional highly cationic alkyl quaternary short chain protein derivatives which combine in one molecule a low molecular weight collagen hydrolysate, fatty radicals and quaternary groups. The low molecular weight parent hydrolysate is prepared such that the basic amino groups in collagen (arginine, histidine, lysine, etc.) are available for quaternization. A pictorial representation of these compounds is as follows:

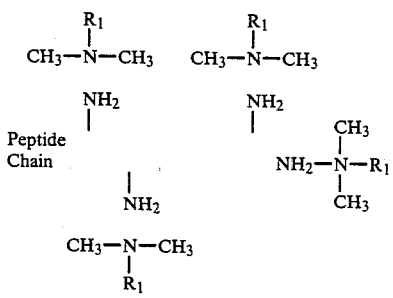

where for laurdimonium $R_1$ is a $C_{12}$ fatty radical, for cocodimonium $R_1$ is a $C_{12-18}$ fatty radical and for steardimonium $R_1$ is a $C_{18}$ fatty radical. Laurdimonium hydrolyzed animal collagen, cocodimonium hydrolyzed animal collagen and steardimonium hydrolyzed animal collagen each have an isoionic point of approximately 11 and a pH (10% aqueous solution) of from 4.0 to 5.5. They are sold under the designations respectively Croquat L, Croquat M and Croquat S by Croda Inc. The second quaternary conditioner is employed in the composition at a concentration of from about 0.2 to about 1 percent by weight based on the total weight of the composition.

Buffering Agent

In order to maintain the pH of the composition in the above-specified range, it is necessary to include in those compositions of the invention which employ an alkali metal bisulfite as reducing agent, a buffering agent. The buffering agent is selected from alkali metal carbonate such as sodium or potassium carbonate, alkali metal phosphate, such as mono-, di- or tri- sodium or potassium phosphate or mixtures thereof. When ammonium bisulfite is employed as reducing agent in the composition it has been found that a buffering agent may be dispensed with since such compositions are self-buffering. However, carbonate and phosphate buffering agents may be employed if desired. The buffering agent is employed in the composition in a concentration of from about 0.75 to about 3 percent by weight based on the weight of the composition.

The final essential ingredient of the composition is water, preferably deionized water. The water is added to the other essential ingredients and any optional ingredients, described hereinafter, in a concentration sufficient to make 100%.

Optional Ingredients

The composition of the invention may include effective amounts of optional ingredients in order to impart additional desirable properties and/or aesthetic appeal to the composition such as additional hair conditioners, preservatives, fragrances, opacifiers, wetting agents, emollients, etc.

As preservatives there may be employed, for example, methylparaben, ethylparaben, or propylparaben, disodium ethylenediaminetetracetic acid (disodium EDTA) and Quaternium-15 (CTFA Adopted Name) and mixtures thereof. Quaternium-15 is defined in the CTFA Dictionery as a quaternary ammonium salt which conforms to the formula:

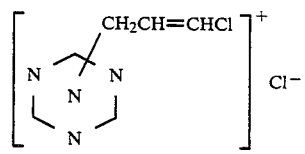

Quaternium-15 is sold under the designation Dowicil 200 by Dow Chemical USA.

The preservatives may be employed in effective amounts as well known in the art, e.g. at a concentration of from about 0.05 to about 0.3 percent by weight of the composition.

It is advantageous to include in the composition TEA-coco-hydrolyzed animal protein (CTFA Adopted Name) since this chemical minimizes hair damage which can occur when hair is contacted with a bisulfite salt. This chemical is defined in the CTFA Dictionary as the triethanolamine salt of the condensation product of coconut acid chloride and hydrolyzed animal protein. It is sold, for example under the designation Lexein ® S-620TA by Inolex Chemicals. This chemical also provides some additional hair conditioning. It may be employed at a concentration of from about 0.25 to about 5 percent by weight of the composition.

It is also advantageous to include in the composition urea which enhances the hair fiber swelling function of the alkanolamine. The urea may be employed at a concentration of from about 5 to about 15 percent by weight of the composition.

As emollients there may be used, for example, lactamide MEA (CTFA Adopted Name) and PEG-150 distearate (CTFA Adopted Name).

Lactamide MEA is lactic acid monoethanolamide. Lactamide MEA is sold under the designation Incromectant LMEA by Croda Surfactants Inc. PEG-150 distearate is defined in the CTFA Dictionary as a polyethylene glycol diester of stearic acid conforming to the formula:

$$CH_3(CH_2)_{16}CO-(OCH_2CH_2)_nO-CO-(CH_2)_{16}CH_3$$

where n has an average value of 150. PEG-150 also adds body, i.e., a nice smooth feel, to the composition. The emollients may be employed at a concentration of from about 0.5 to about 5 percent by weight of the composition.

As opacifiers there may be employed anionic surfactants or a combination of an anionic surfactant with a nonionic surfactant. As anionic surfactant there may be employed for example, sodium laureth sulfate (CTFA Adopted Name) which conforms to the formula (CTFA Dictionary):

$$CH_3(CH_2)_{10}CH_2(OCH_2CH_2)_nOSO_3Na$$

where n averages between 1 and 4. This chemical is sold under the designation Standapol ES by Henkel, Inc.

A further anionic surfactant that may be employed as an opacifier is sodium trideceth-7 carboxylate (CTFA Adopted Name) conforming to the formula (CTFA Dictionary):

$$CH_3(CH_2)_{11}CH_2(OCH_2CH_2)_6OCH_2COONa$$

This chemical is sold under the designation Sandopan DTC by Sandoz, Inc. Colors and Chemicals Division.

The opacifiers may be employed in the composition in a concentration of from about 0.5 to about 1.5 percent by weight of the composition.

The compositions may be formulated as lotions, mousses, gels, creams or aerosols. When the essential ingredients are mixed in the concentrations specified herein before, they are obtained either as dispersions in the form of lotions or gels. A gel can be obtained if the guar hydroxypropyltrimonium chloride is used in a concentration falling at the upper end of the specified concentration range, i.e., from about 1.4 to 1.5 weight per cent, while a lotion (liquid) can be obtained at lower concentrations of the guar hydroxypropyltrimonium chloride. The composition can be obtained in the form of a cream by adding thereto an effective amount of an opacifier as described herein before, i.e., at a concentration of from about 0.5 to about 1.5 percent by weight. The composition in the form of a liquid can be formulated as an aerosol which, on dispensing from a conventional aerosol dispenser, is obtained in the form of a creamy foam known in the art as a mousse. Such compositions include conventional aerosol propellants, such as a hydrocarbon, for example isobutane, or a halocarbon, for example 1,1-difluoroethane, and mixtures thereof, in amounts effective to permit substantially complete evacuation of the composition from the aerosol container. The amount of any particular aerosol propellant or mixture of propellants to be employed can readily be determined by one of ordinary skill in the art.

The composition of the invention preferably is applied to damp hair, e.g., after a shampoo and towel drying. The composition then is worked into and evenly distributed throughout the hair by massage (shampooing) until a thick foam results. The foam is essential for achieving maximum enhanced body and volume of the hair. Thus when in the method of the invention the hair is lifted away from the scalp, the foam functions to maintain the hair in the lifted position throughout the entire time the composition remains in contact with the hair. This results in an unexpected increase in the body and volume of hair over and above that which results solely from the swelling of the hair fiber if left to lie flat against the scalp and precludes the need for rollers and rods. However, if the composition is in gel form, foaming, although preferred, is not essential since the gel as such can maintain the hair in the lifted position. If desired, a plastic cap may be used to cover the hair after it has been treated with the composition and lifted in order to hasten the body enhancing process. Since the ruptured disulfide linkages in the hair can be allowed to reform by air oxidation rather than the use of a neutralizer such as hydrogen peroxide, the method of the invention provides a convenient one-step procedure for enhancing the body of hair. The air oxidation preferably is accelerated by blow drying the hair at elevated temperatures using conventional blow drying techniques. Of course, if desired, the hair may, after completion of the method of the invention, be treated with a suitable oxidizing agent such as hydrogen peroxide in order to eliminate slight odors which may be imparted to the hair during the cleaving of the disulfide linkages by the reducing agent. However, such odors as may be present on the hair generally will dissipate naturally at ambient temperatures in about 24 hours after treatment.

Lifting of the hair in the method of the invention can be accomplished by such means as the finger tips, a plastic hair pick or the tail of a comb, the lifting being performed on portions of the hair comprising strands of hair in various numbers. Using such means, the hair may, according to individual tastes, be lifted in straight form, or shaped gently, for example, into bends, waves or curls. If desired, plastic clips may be employed. In the case of long hair, the hair can be loosely piled on top of the head and secured with plastic clips. It will be understood that the term lifting the hair as used herein means lifting the hair in either straight or shaped (e.g., bent, waved or curled) configuration without the use of rods or curlers.

On completion of the method of the invention the hair may be shampooed with a conventional shampoo (which may contain a small amount of hydrogen peroxide) to give the perception of cleaner hair and to help remove any residual odor. The hair then may be styled in any desired fashion without any perceived loss of enhanced body.

The enhanced body imparted to the hair by the method of the invention is perceived by the consumer to remain with the hair for a period of from about 4 to 6 weeks, even with repeated shampooings and stylings.

The compositions, when used in accordance with the method of the invention, are retained on the hair, after having been distributed evenly throughout the hair as a foam, for from about 20 to about 30 minutes, the latter time in the case of "normal" hair and for shorter periods, down to about 20 minutes, for hair which has been recently colored, the timing being dependent on how recently the coloring was performed.

The compositions of the invention are adapted for use on human hair in the home as well as in beauty salons.

The compositions may be formulated at ambient temperatures by combining the ingredients thereof in any order using conventional mixing techniques such as stirring. A convenient process is as follows (stirring maintained throughout the process):

The hydroxypropyltrimonium chloride is added to the water and after 15 to 20 minutes the bisulfite salt is added. After about 5 minutes there are added in sequence the alkanolamine, the carbonate (or phosphate), the carbonate being added at a rate to avoid excess foaming, and finally the quaternary ammonium compound (conditioning agent). Any optional ingredients may be added at the end of the process or at intermediate stages thereof. Stirring is then continued for about 15 minutes after which the process is completed.

The compositions may be packaged in and dispensed from conventional packages and dispensers such as aerosol dispensers (in combination with a aerosol propellant system) or, such as in the case of gels, squeeze tubes, or, such as in the case of liquids, squeeze bottles, such dispensers having or being fitted with suitable dispensing openings as are conventional in the art.

The following examples are illustrative of the compositions of the invention without, however, being limited thereto.

Specific compositions with varying concentrations of ingredients falling within the ranges of weight-percent concentrations specified for Examples I, II and III in the table below were formulated:

| Ingredient | Weight-Percent[a] Example: | | |
|---|---|---|---|
| | I | II | III |
| Sodium bisulfite | 5.0–10.0 | 5.0–10.1 | — |
| Ammonium bisulfite | | | 6.75–9.0 |
| Monoethanolamine | q.s. to pH 6.8–10[b] | | |
| Guar hydroxypropyltrimonium chloride | 0.1–1.5 | | |
| Quaternary compound of Formula I | 0.1–0.50 | — | 0.1–0.50 |
| Laurdimonium(or cocodimonium or steardimonium)hydrolyzed animal collagen | | 0.08–0.60 | |
| Sodium carbonate | 0.75–2.0 | 0.75–2.0 | — |
| Ammonium carbonate | — | — | 1.0–3.0 |
| Urea | | 5.0–15.0 | |
| TEA-coco-hydrolyzed animal protein | 0.08–0.80 | — | 0.08–0.80 |
| Sodium laureth sulfate or sodium trideceth-7 carboxylate | — | 0.5–1.5 | 0.5–1.5[c] |
| PEG-150 distearate or lactamide MEA | — | 1.0–5.0 | — |
| Deionized water | q.s. to 100%[d] | | |

[a]Based on 100% active ingredient
[b]Approximately 2.0–5.0 wt %
[c]Sodium laureth sulfate
[d]Approximately 65–85 wt %

The following specific examples were prepared:

Example IV

| Ingredient | Weight % |
|---|---|
| Sodium bisulfite | 7.70 |
| Monoethanolamine | 3.94 |
| Guar hydroxypropyltrimonium chloride[a] | 0.20 |
| Quaternary compound of Formula I[b] | 0.50 |
| Sodium carbonate | 1.50 |
| TEA-coco-hydrolyzed animal protein[c] | 0.80 |
| Deionized water | 85.36 |
| pH 8.2 | |
| | 100.00 |

[a]Jaquar C-17
[b]Dehyquart SP
[c]Lexein ® S-620TA

The composition of Example IV was formulated as an aerosol having the following composition:

| Composition of Example IV | 90.5 wt % |
|---|---|
| Propellant | 9.5 wt % |

The propellant consisted of 60 parts by weight of isobutane and 40 parts by weight of 1,1-difluoroethane (HYDROFLUOROCARBON 152A).

The aerosol composition when dispensed from a conventional aerosol container fitted with an appropriate dispensing button is in the form of a mousse.

When used on human subjects having fine, normal and coarse hair in accordance with the method of the invention, the aerosol composition substantially enhanced the body (fullness and volume) as well as the manageability of the hair in most cases.

Examples V and VI are as follows:

| Ingredient | Weight % | |
|---|---|---|
| | V | VI |
| Sodium bisulfite | 8.60 | — |
| Ammonium bisulfite | — | 9.00 |
| Monoethanolamine | 2.80 | 2.20 |
| Guar hydroxypropyltrimonium chloride[a] | 0.20 | 0.20 |
| Quaternary Compound of Formula I[b] | 0.25 | 0.25 |
| Sodium carbonate | 1.40 | — |
| Urea | 5.00 | 5.00 |
| TEA-coco hydrolyzed animal protein[c] | 0.80 | 0.80 |
| Fragrance | 0.50 | 0.50 |
| Quaternium-15[d] | 0.10 | 0.10 |
| Methylparaben | 0.10 | 0.10 |
| Disodium EDTA | 0.02 | 0.02 |
| Deionized water | q.s. to 100% | |
| pH | approx. 7.4 | approx 6.8 |

[a],[b] and [c] see Example IV
[d]Dowicil 200

In each of Examples IV, V and VI the weight-percent is based on 100% active ingredient.

The compositions of Examples I to VI were formulated according to the process described herein before. In Example I the urea was added immediately after the monoethanolamnne and the TEA-coco-hydrolyzed animal protein was added immediately after the carbonate. In Example II the urea was added after the guar hydroxypropyltrimonium chloride and the lactamide MEA or PEG-150 distearate and the sodium laureth sulfate or sodium trideceth-7 carboxylate were added in sequence immediately after the quaternary ammonium compound. In Example III the TEA-coco-hydrolyzed animal protein, the sodium trideceth-7 carboxylate and the urea were added in sequence after the guar hydroxypropyltrimonium chloride. In Example IV the TEA-coco-hydrolyzed animal protein was added after the bisulfite. In Examples and V and VI the urea was added after the guar hydroxypropyltrimonium chloride, the TEA-coco-hydrolyzed animal protein after the bisulfite and the fragrance and preservatives, in the sequence indicated, at the end.

What is claimed is:

1. A method for enhancing the body of hair comprising in sequence the following steps:
  (1) applying to the hair a composition comprising:
    (a) from about 5 to about 10 percent by weight of an alkali metal bisulfite or ammonium bisulfite;
    (b) from about 2 to about 5 percent by weight of monoalkanolami dialkanolamine or trialkanolamine wherein the alkanol radical in each instant has from 1 to 3 carbon atoms;

(c) from about 0.1 to about 1.5 percent by weight of guar hydro chloride;
(d) from about 0.2 to about 1 percent by weight of a quaternary ammonium compound selected from the group consisting of a compound conforming to the formula:

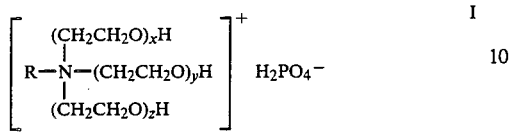

wherein x+y+z has an average value of 10 and R is a straight-chain alkyl radial having from 16 to 18 carbon atoms and mixtures of said radicals; laurdimonium hydrolyzed animal collagen, cocodimonium hydrolyzed animal collagen and steardimonium hydrolyzed animal collagen; and
(e) water sufficient to make 100%; provided that when (a) is an alkali metal bisulfite, the composition additionally comprises:
(f) from about 0.75 to about 3 percent by weight of an alkali metal carbonate, ammonium carbonate or an alkali metal phosphate;
(2) working the composition into the hair until the composition is distributed throughout the hair;
(3) lifting the hair;
(4) allowing the composition to remain in contact with the hair for from about 20 to about 30 minutes;
(5) rinsing the hair with water sufficient to remove the composition from the hair; and
(6) drying the hair.

2. The method of claim 1 wherein the composition is selected from the group consisting of:
(i) a composition consisting essentially of 8.60 weight-percent of sodium bisulfite, 2.80 weight-percent of monoethanolamine, 0.20 weight-percent of quar hydroxypropyltrimonium chloride, 0.25 weight-percent of the quaternary ammonium compound of Formula I, 1.40 weight-percent of sodium carbonate, 5.00 weight-percent of urea, 0.8 weight-percent TEA-coco-hydrolyzed animal protein, 0.50 weight-percent of a fragrance, an effective amount of a preservative and the remainder to 100% water; and
(ii) a composition consisting essentially of 9.00 weight-percent of ammonium bisulfite, 2.20 weight-percent of monoethanolamine, 0.20 weight-percent of guar hydroxypropyltrimonium chloride, 0.25 wight-percent of the quaternary ammonium compound of Formula I, 5.00 weight-percent of urea, 0.80 weight-percent of TEA-coco-hydrolyzed animal protein, 0.50 weight-percent of a fragrance, an effective amount of a preservative and the remainder to 100% water.

3. The method of claim 2 wherein the preservative consists essentially of a combination of 0.10 weight-percent of Quaternium-15, 0.10 weight-percent of methylparaben and 0.02 weight-percent of disodium EDTA.

4. The method of claim 1, wherein the composition is applied in the form of a mousse.

5. The method of claim 1, wherein the lifting of the hair comprises lifting portions of the hair in straight, bent or curled form.

6. The method of claim 5 wherein the hair is lifted by means of the finger tips, a hair pick or the tail of a comb.

7. The method of claim 1, wherein the hair is air-dried at ambient temperatures.

8. The method of claim 1, wherein the hair is dried at elevated temperatures.

9. The method of claim 1 wherein the composition is in the form of a lotion, cream or gel and is worked into the hair until a foam results throughout the hair.

10. A method for enhancing the body of hair comprising in sequence the following steps:
(1) applying to the hair a composition selected from the group consisting of:
(i) a composition consisting essentially of from 5.0 to 10.0 weight-percent of sodium bisulfite, from 2.0 to 5.0 weight-percent of monoethanolamine, from 0.1 to 1.50 weight-percent of guar hydroxypropyltrimonium chloride, from 0.1 to 0.50 weight-percent of the quaternary ammonium compound of Formula I, from 0.75 to 2.0 weight-percent of sodium carbonate, from 5.0 to 15.0 weight-percent of urea, from 0.08 to 0.80 weight-percent of TEA-coco-hydrolyzed animal protein and the remainder to 100% water;
(ii) a composition consisting essentially of from 5.0 to 10 1 weight-percent of sodium bisulfite, from 2.0 to 5.0 weight-percent of monoethanolamine, from 0.1 to 1.5 weight-percent of guar hydroxypropyltrimonium chloride, from 0.08 to 0.60 weight-percent of laurdimonium hydrolyzed animal collagen, cocodimonium hydrolyzed animal collagen or steardimonium hydrolyzed animal collagen, from 0.75 to 2.0 weight-percent of sodium carbonate, from 5.0 to 15.0 weight-percent of urea, from 0.5 to 1.5 weight-percent of sodium laureth sulfate or sodium trideceth-7 carboxylate, from 1.0 to 5.0 weight-percent of PEG-150 distearate or lactamide EA and the remainder to 100% water;
(iii) a composition consisting essentially of from 6.75 to 9.0 weight-percent of ammonium bisulfite, from 2.0 to 5.0 weight-percent of monoethanolamine, from 0.1 to 1.5 weight-percent of guar hydroxypropyltrimonium chloride, from 0.1 to 0.50 weight-percent of the quaternary ammonium compound of Formula I, from 1.0 to 3.0 weight-percent ammonium carbonate, from 5.0 to 15.0 weight-percent of urea, from 0.08 to 0.8 weight-percent of TEA-coco-hydrolyze animal protein, from 0.5 to b 1.5 weight-percent of sodium laureth sulfate and the remainder to 100% water; and
(iv) a composition consisting essentially of 7.70 weight-percent of sodium bisulfite, 3.94 weight-percent of monoethanolamine, 0.20 weight-percent of guar hydroxypropyltrimonium chloride, 50 weight-percent of the quaternary ammonium compound of Formula I, 1.50 weight-percent of sodium carbonate, 0.80 weight-percent of TEA-coco-hydrolyzed animal protein and the remainder to 100% water;
(2) working the composition into the hair until the composition is distributed throughout the hair;
(3) lifting the hair;
(4) allowing the composition to remain in contact with the hair for from about 20 to about 30 minutes;
(5) rinsing the hair with water sufficient to remove the composition from the hair; and
(6) drying the hair.

* * * * *

UNITED STATES PATENT AND TRADEMARK OFFICE
CERTIFICATE OF CORRECTION

PATENT NO. : 4,847,076

DATED : July 11, 1989

INVENTOR(S) : V.M. Deshpande, J.M. Walts & S.A. Decker

It is certified that error appears in the above-identified patent and that said Letters Patent is hereby corrected as shown below:

Column 4, line 16, "about to" should read --about 2 to--; line 35, "backone" should read --backbone--; lines 42, 43, 45 and 46, "∿" should read --@--, each instance.

Column 5, line 12, "straightchain" should read --straight-chain--; lines 33-45,

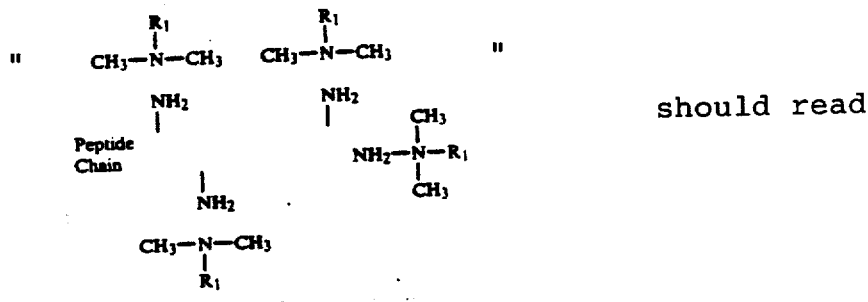

should read

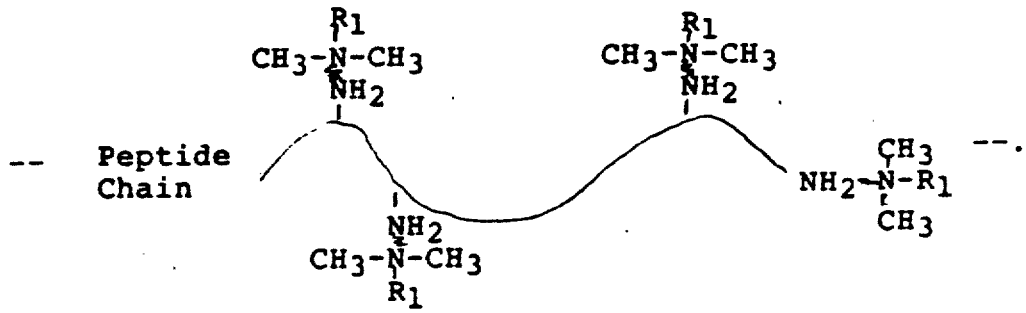

UNITED STATES PATENT AND TRADEMARK OFFICE
CERTIFICATE OF CORRECTION

PATENT NO. : 4,847,076

DATED : July 11, 1989

INVENTOR(S) : V.M. Deshpande, J.M. Walts & S.A. Decker

It is certified that error appears in the above-identified patent and that said Letters Patent is hereby corrected as shown below:

Column 6, lines 30-37,

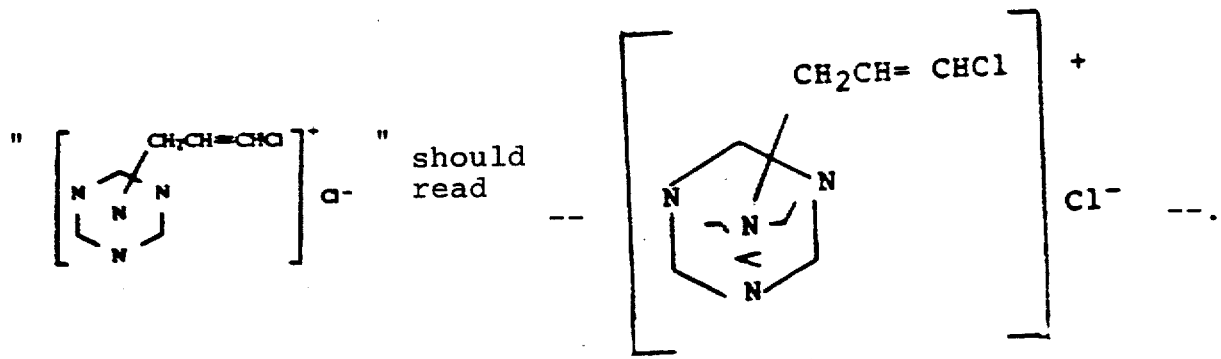

Column 10, line 42, "monoethanolamnne" should read --monoethanolamine--; line 66, Claim 1, "monoalkanolami" should read --monoalkanolamine,--.

Column 11, line 2, Claim 1, "hydro" should read --hydroxypropyltrimonium--; line 15, Claim 1, "radial" should read --radical--; line 52, Claim 2, "wight-percent" should read --weight-percent--.

UNITED STATES PATENT AND TRADEMARK OFFICE
CERTIFICATE OF CORRECTION

PATENT NO. : 4,847,076
DATED : July 11, 1989
INVENTOR(S) : V.M. Deshpande, J.M. Walts & S.A. Decker It is certified that error appears in the above-identified patent and that said Letters Patent is hereby corrected as shown below:

Column 12, line 24, Claim 10, "10 1" should read --10.1--; line 36, Claim 10, "EA" should read --MEA--; line 47, Claim 10, "-hydrolyze" should read -- -hydrolyzed--; line 48, Claim 10, "to b 1.5" should read --to 1.5--; line 55, Claim 10, "50" should read --0.50--.

Signed and Sealed this

Eighth Day of January, 1991

Attest:

HARRY F. MANBECK, JR.

*Attesting Officer*     *Commissioner of Patents and Trademarks*